United States Patent [19]

Smith et al.

[11] Patent Number: 4,968,625
[45] Date of Patent: Nov. 6, 1990

[54] CENTRIFRUGATION VIAL AND CLUSTER TRAY

[75] Inventors: Jerry W. Smith, Ann Arbor; Deborah R. Siena, Willis, both of Mich.

[73] Assignee: Difco Laboratories, Detroit, Mich.

[21] Appl. No.: 349,193

[22] Filed: May 9, 1989

Related U.S. Application Data

[63] Continuation-in-part of Ser. No. 150,630, Feb. 1, 1988, Pat. No. 4,829,006.

[51] Int. Cl.⁵ ............................................... C12M 1/20
[52] U.S. Cl. ................................. 435/301; 220/23.4; 220/355
[58] Field of Search ............... 435/300, 301, 287, 296; 220/23.4, 23.8, 355

[56] References Cited

U.S. PATENT DOCUMENTS

| | | | |
|---|---|---|---|
| 3,446,391 | 5/1969 | Yates | 220/355 |
| 3,977,563 | 8/1976 | Holt | 220/355 |
| 4,358,539 | 11/1982 | Bittings | 435/301 |
| 4,735,778 | 4/1988 | Manyama et al. | 435/301 |
| 4,786,601 | 11/1988 | Rothenberg | 435/301 |

FOREIGN PATENT DOCUMENTS 128778 12/1984 European Pat. Off. .

*Primary Examiner*—Carroll B. Dority
*Attorney, Agent, or Firm*—Harness, Dickey & Pierce

[57] ABSTRACT

A plurality of centrifugation vials having a common base form a cluster tray suitably shaped for receipt by a standard multiwell or cluster tray carrier for a centrifuge. The tray base is segmented into individual vial bases to facilitate separation of a given vial from the cluster tray if desired. The bottom surface of each vial directly under the vial's interior chamber is recessed from the bottom supporting surface of the cluster tray to avoid scuffing or scratching. A skirted snap-plug cap is also provided for improved sealing means and to decrease the risk of contamination upon opening and closing of the vial. The vials and cluster trays thereof are preferably formed from transparent polymeric materials which can support anchored cell growth.

17 Claims, 3 Drawing Sheets

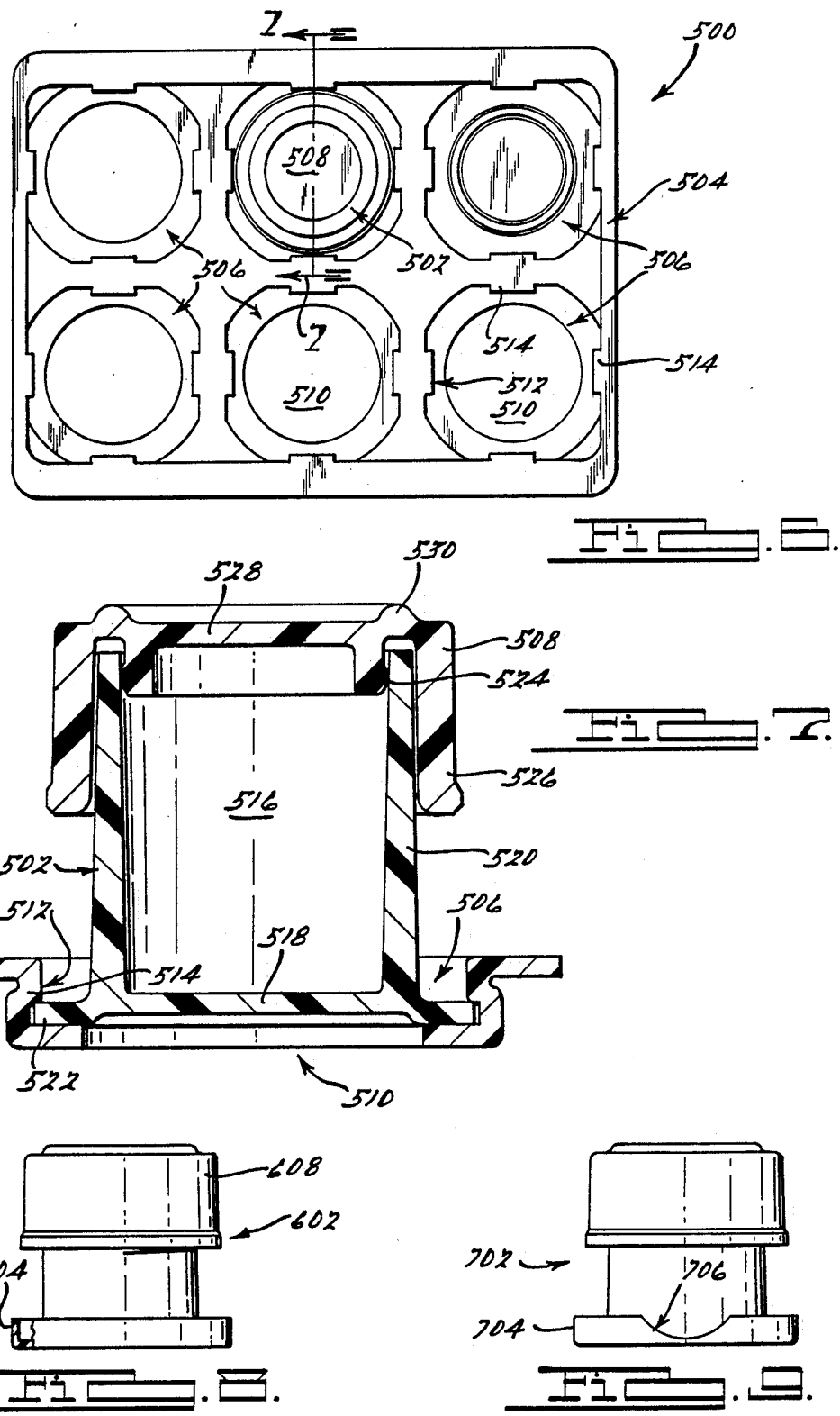

CENTRIFUGATION VIAL AND CLUSTER TRAY

REFERENCE TO RELATED APPLICATION

This application is a continuation-in-part application of U.S. application Ser. No. 150,630 filed Feb. 1, 1988, now U.S. Pat. No. 4,829,006.

BACKGROUND OF THE INVENTION

The present invention relates generally to diagnostic and laboratory ware adapted for centrifugation. More specifically, the invention pertains to centrifugation vials and integrated yet severable arrays thereof.

Culture vials amenable to centrifugation, such as conventional culture tubes, free-standing shell vials and cluster trays of vials, have generally tube-shaped chambers wherein specimens can be placed or cells cultured. Some vial cluster trays feature independent arrangements or removable strips of vials to permit the use or processing of less than the whole tray of vials. Conventional vials and cluster trays are most often constructed of glass or transparent plastic materials such as polystyrene to enable viewing of the vial contents. Plug or snap-type closures constructed of translucent or opaque materials are also often provided with the vials to seal their contents from the environment.

Conventional individual vials are, however, disadvantageous in that the vial chambers are generally of a depth non-amenable to facile user handling or treatment of the vial contents. The construction of free-standing vials and cluster trays with removable vials is also such that the bottom surfaces of the vials contact the surface upon which they rest, leading to scratching or scuffing of the bottom surfaces and impeding examination of the contents. Additionally, the materials of which vials and trays are constructed often will not support anchored cell culture, at least not without pretreatment of the vial surface. In addition, the plug or snap closures generally provided with conventional vials often splatter the vial contents upon removal of the closure from the vial thus increasing the risk of contamination. Skirted caps as an alternative often fail to provide adequate closure of the vial chamber.

Thus, it would be desirable to provide vials or cluster trays thereof amenable to centrifugation having chambers of a depth facilitating handling and treatment of the contents. It would also be desirable for the trays of vials to have convenient means for detaching or removing any number of individual vials from the tray. It would further be desirable to provide free-standing vials and trays with a construction preventing scratching or scuffing of the vial bottoms. It would also be desirable to provide vials and trays constructed of materials that support cell anchorage and whose vial bottoms can be easily detached so that cells cultured thereon can be directly viewed or treated. Moreover, it would be desirable to provide an improved closure for centrifugation vials and trays with adequate sealing capability but which minimize the risk of splatter and contamination upon removal from the vial.

SUMMARY OF THE INVENTION

The present invention provides a centrifugation vial and a cluster tray arrangement thereof. The cluster tray is designed so that individual free-standing vials can be easily severed or separated from the tray prior to or after specimens or reagents have been placed in the vial. Hence, the vials of the present invention may be used individually or as trays of severable or separated vials.

The interior chamber of an individual vial of the present invention is defined by a generally cylindrical side wall and a bottom wall and is of a depth which facilitates the handling or treatment of the vial contents. The bottom is raised from the surface supporting the vial to avoid scuffing or scratching so that the contents of the vial may be microscopically or directly examined without view-disturbing marks. In one embodiment, the vial bottom is constructed of a sufficient thinness to enable it to easily cut away from the remainder of the vial body for staining or microscopic viewing. The vial is preferably also constructed of transparent material which will support anchored cell growth so that the vial can be used for the culture of anchorage-dependent cells if so desired.

The vial of the present invention further includes an improved skirted locking cap which decreases the likelihood of contamination of either the handler or the vial contents. The construction of the improved cap for the vial of the invention also permits shipping of the vial and any contents therein with a decreased risk of spillage. Additionally, the cluster tray of the invention is provided with a tray cover which helps decrease cross-contamination between vials and has stacking means.

Another feature of the present invention is that the cluster tray of vials of the invention may be formed in an arrangement to fit standard tray carriers for centrifuges currently in use. With appropriate adapters, individual vials separated form the tray can also be centrifuged.

These and other features of the invention will become apparent from a reading of the detailed description of the preferred embodiments taken in conjunction with the drawings described below.

BRIEF DESCRIPTION OF THE DRAWINGS

FIG. 6 is a top plan view of an alternative preferred embodiment of a cluster tray of the present invention having removable vials.

FIG. 7 is a cross-sectional view taken along line 6—6 of the cluster tray of FIG. 6.

FIG. 8 is a side elevational view of an alternative embodiment of a removable vial and cap for use with the cluster tray base of FIG. 6.

FIG. 9 is a side elevational view of another alternative embodiment of a removable vial and cap for use with the cluster tray base of FIG. 6.

DETAILED DESCRIPTION OF THE PREFERRED EMBODIMENTS

Figure 1:
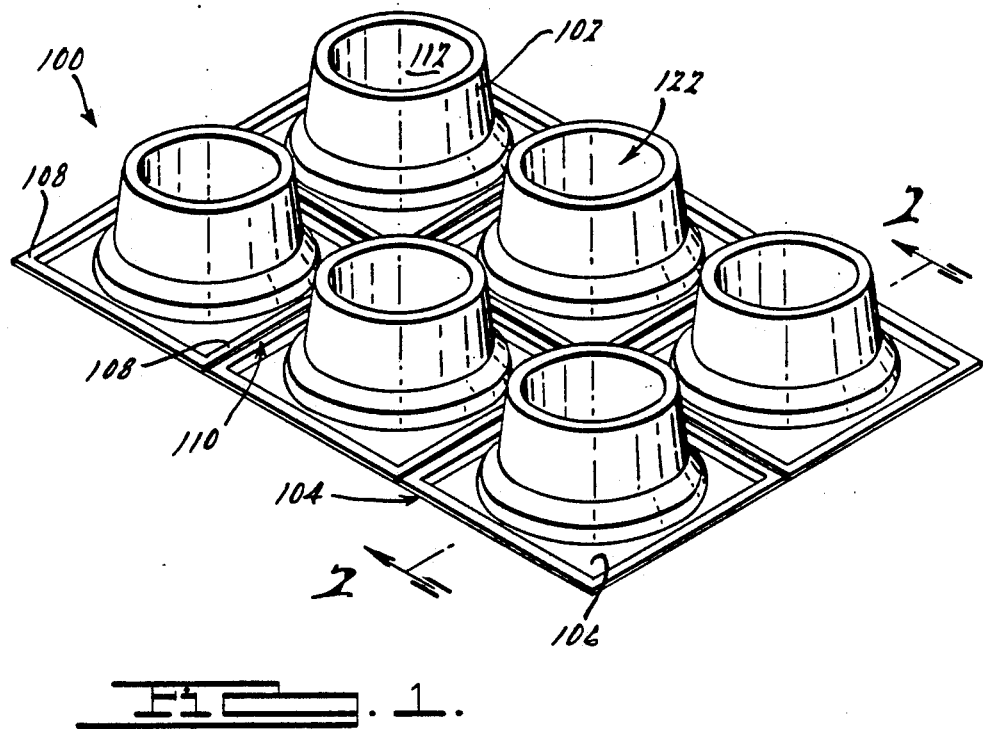
FIG. 1 is a perspective view of a preferred embodiment of a cluster tray of vials arranged in accordance with the principles of the invention.

Referring now to FIG. 1, a preferred embodiment of the cluster tray of vials of the present invention is shown in perspective and indicated generally by the numeral 100. As shown in FIG. 1, cluster tray 100 comprises six similarly-formed vials 102, each integrally formed with a cluster tray base 104. It should be appreciated, however, that although six vials are depicted in this embodiment, tray 100 can be formed with any suitable number of vials.

As shown in FIG. 1, tray base 104 is segmented into vial base regions 106 corresponding to each of the vials of the tray. Tray base 104 and each vial base region 106 is bounded by a raised lip 108 which serves to reinforce the tray and function as a cutting guide between individual vials. Lip 108 between adjacent vial base regions is preferably indented, perforated or scored, as at 110, to further facilitate separation of individual vials from the remainder of the tray base. In this manner, any of the vials are easily severed for individual use from the remainder of the cluster tray.

Figure 2:
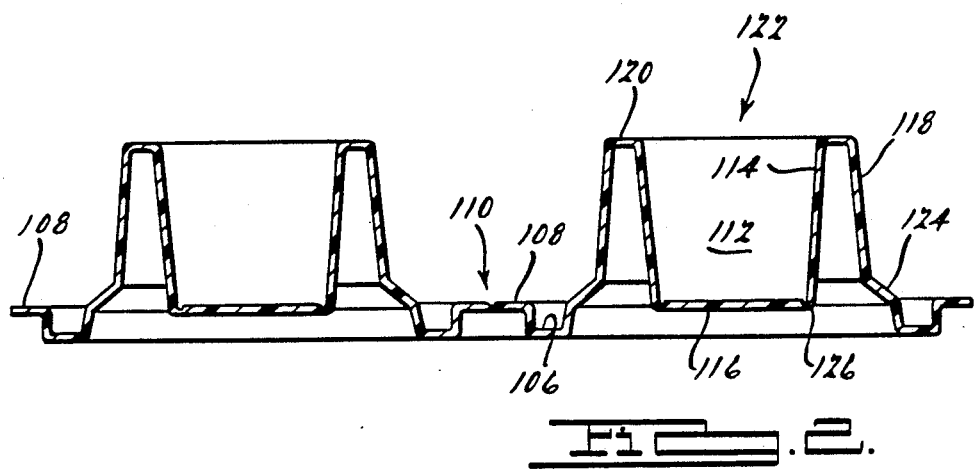
FIG. 2 is a cross-sectional view taken along line 2—2 of the cluster tray of FIG. 1.

Referring now to FIG. 2, a cross-section view of cluster tray 100, each vial 102 of tray 100 is provided with a vial chamber 112. Vial chamber 112 is defined by an inner vial wall 114 extending upwardly from and integrally formed with a vial bottom wall 116. Inner vial wall 114 extends upwardly to meet outer vial wall 118, their juncture forming an annular vial rim 120 surrounding vial chamber opening 122. Vial outer wall 118 extends downwardly and outwardly to form a vial shoulder 124. Vial shoulder 124 reinforces each vial unit, and, optionally, can provide a cap skirt rest if a skirted cap is used to seal the vial chamber opening. Vial shoulder 124, in turn, extends outwardly and is integrally formed with its corresponding vial base region 106 of tray base 104.

In the preferred embodiment set forth in FIGS. 1 and 2, outer wall 118 slopes away from the vial top at an angle of approximately 3°, while inner wall 114 slopes in a direction opposite to that of outer wall 118 at an angle of approximately 7°. However, it should be appreciated that the angle and direction of slope of the walls or straight unsloped walls can be employed within the broad scope of this invention. Additionally, the depth of vial chamber 112 is relatively shallow as opposed to conventional culture tubes and shell vials and holds approximately 1–2 ml of liquid with adequate head space.

Referring again to FIG. 2, bottom wall 116 of vial chamber 112 is offset from the bottom surface of tray base 104 in such a manner to avoid scuffing or scratching of the exterior surface of bottom wall 116 whether the vial is attached to tray base 104 or is severed and free-standing. This feature enables viewing of vial contents supported on the interior surface of bottom wall 116 without view-obstructing scratches or scuff marks.

Bottom wall 116 of vial 102 is preferably constructed of sufficient thinness to enable relatively easy removal under mechanical force of the bottom section of the chamber for treatment, viewing or any other desired processing of a specimen thereon. Vial bottom wall 116 is optionally provided with a circumferential groove, as at 126, or other separating means such as perforations or indentations, to facilitate detachment of the vial bottom wall from the rest of the vial is so desired. Detachable vial bottom walls can thus take the place of coverslips which are currently used in culture vials. It should be appreciated, however, that coverslips may also be used in conjunction with the vial of the present invention.

Figure 3:
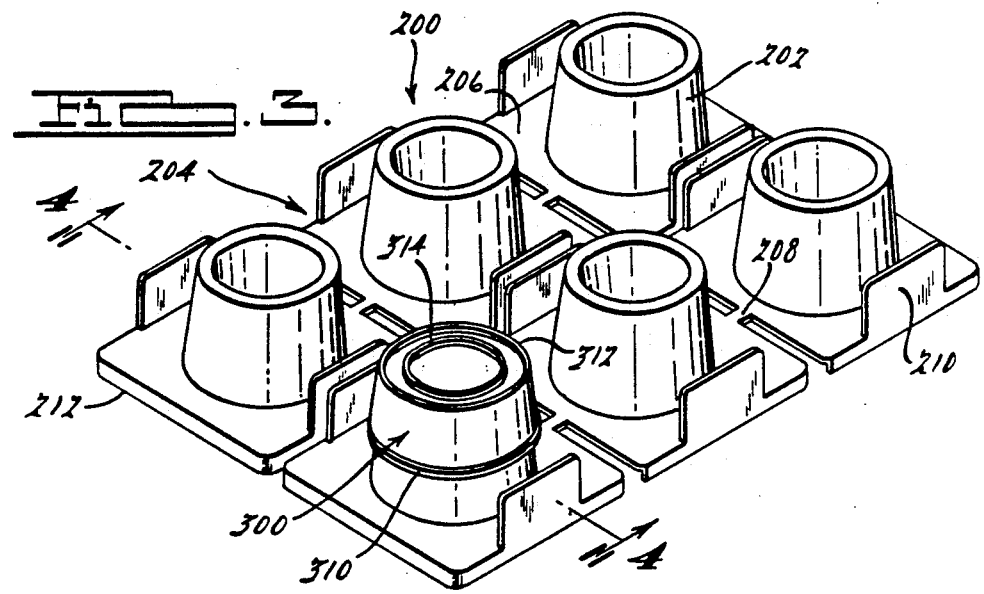
FIG. 3 is a perspective view of another preferred embodiment of a cluster tray of vials arranged in accordance with the principles of the invention.

Referring now to FIG. 3, a perspective view of another preferred embodiment of the cluster tray of the invention is shown and indicated generally by the numeral 200. Cluster tray 200 generally comprises six similarly-shaped vials 202, each integrally formed with a tray base 204. Tray base 204 is segmented into physically discrete vial base regions 206 each of which is joined to the vial base region adjacent thereto by a connector 208. It should be appreciated that although segmentation of tray base 204 in FIG. 3 is accomplished by physical separation, segmenting can also be achieved by a variety of alternative methods, i.e. perforation, scoring, or indentation.

As shown in FIG. 3, each vial 202 of tray 200 is also provided with a pair of opposing tabs 210 integrally formed with and projecting upwardly from the periphery of vial base region 206 to assist in the handling of the vial. Tray 200 further includes a nesting lip 212 integrally formed with and extending downwardly from the outer periphery of tray base 204 to facilitate the stacking of trays for shipping or storage.

Figure 4:
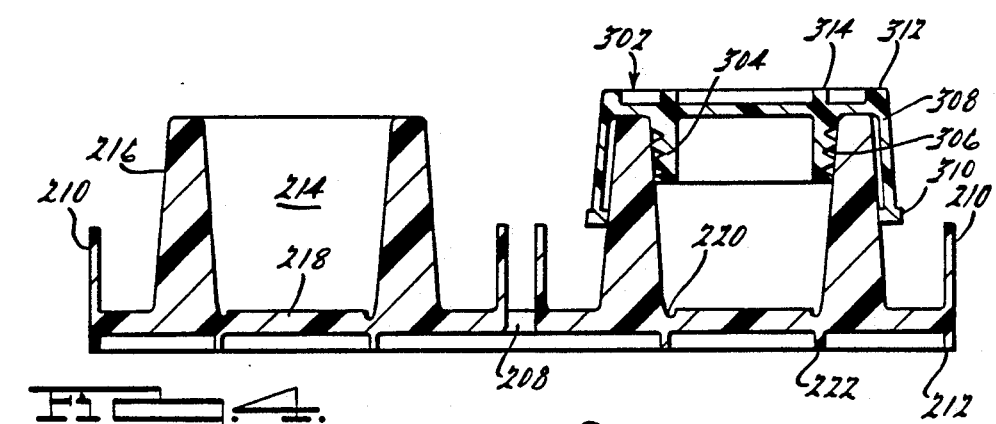
FIG. 4 is a cross-sectional view taken along line 4—4 of the cluster tray of FIG. 3.

Referring now to FIG. 4, a cross-section view of tray 200 of FIG. 3, each vial 202 of cluster tray 200 includes a vial chamber 214 defined by a vial side wall 216 integrally formed with and extending upwardly from a vial bottom wall 218. Vial bottom wall 218 is also preferably provided with a circumferential groove, as at 220, or other separating means to facilitate detachment of the vial bottom wall if so desired.

To prevent scuffing of the exterior surface of vial bottom wall 218, bottom wall 218 of each vial 202 is provided with offsetting means generally comprising an antiscuff ring 222 to offset the vial's bottom surface from the surface upon which it rests. However, although offsetting means for vial 202 comprises an antiscuff ring, it should be appreciated that other suitable means for offsetting the vial bottom surface from a supporting surface can be employed. For example, the bottom surface of the vial bottom wall can be offset from the bottom surface of the tray base by decreasing the vial bottom wall thickness relative to the tray base thickness or by simply elevating the position of the vial bottom wall relative to the tray base as in cluster tray 100 of FIG. 2.

Returning now to FIGS. 3 and 4, the vial of the present invention is also provided with a locking cap 300. As shown in these Figures, cap 300 generally comprises a top portion 302 from which extends a sealing plug portion 304. As shown particularly in FIG. 4, an annular undersurface of top portion 302 preferably forms a bearing surface engaging the vial rim surrounding the opening of the vial chamber. The outer surface of plug portion 304 is shaped for close engagement with the inner wall of the vial chamber and preferably includes concentric ribs or O rings, as at 306, to enhance engagement of cap 300 with the vial.

Referring again to FIGS. 3 and 4, cap 300 further comprises a circumferential cap skirt 308 extending from top portion 302 and spaced from sealing plug portion 304. As shown in FIG. 4, inner surface of the cap skirt preferably engages at least a portion of the outer surface of the vial wall. Cap skirt 308 reduces splatter when cap 300 is removed and affords improved protection of the user and vial contents when opening and closing the vial chamber using the locking cap 300. In addition, the bottom edge of cap skirt 308 preferably extends past the bottom of sealing plug portion 304. Thus, upon placement of cap 300 on a planar supporting surface, plug portion 304 will not contact the supporting surface, thereby reducing the risk of contamination.

As shown in FIGS. 3 and 4, cap skirt preferably includes a cap lip 310 extending outwardly from its bottom edge to facilitate removal and replacement of cap 300 and a circumferential stiffening ring 312 to impart rigidity to the cap. Additionally, cap 300 is preferably provided with a cap ring 314 on the outer surface of top portion 302 to prevent marring of the outer surface of cap top portion with view-disturbing marks. When used in conjunction with vials having antiscuff rings 222 on their bottom surface, cap ring 314 and the antiscuff ring further provide stacking means by the telescoping of the antiscuff ring over cap ring 314 when capped vials or trays thereof are stacked.

Figure 5:
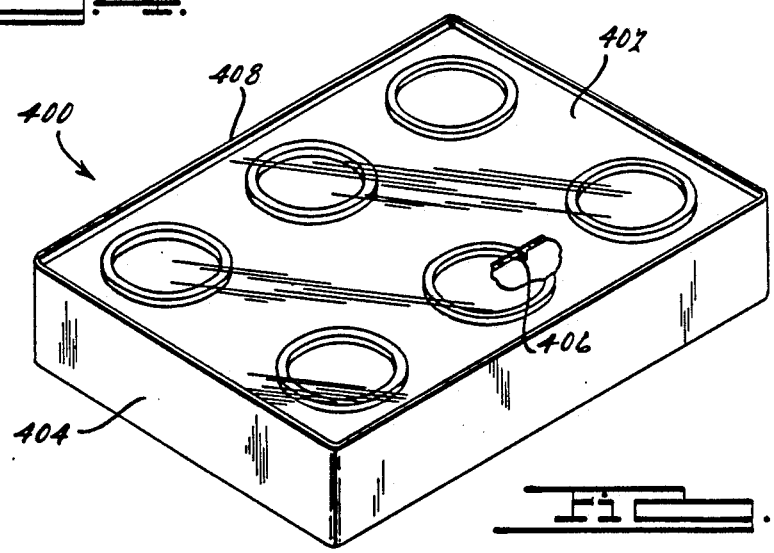
FIG. 5 is a perspective view partially in section of a preferred embodiment of the tray cover of the present invention.

Referring now to FIG. 5, a tray cover for the cluster tray of the present invention is shown and indicated generally by the numeral 400. Tray cover 400 is generally comprised of a substantially planar base 402 and four cover walls 404. Tray cover 400 includes a plurality of vial rings 406 extending from its inner surface which generally correspond in size, number and position with the vials of the tray for which it is designed. Although tray cover 400 can be used in conjunction with individual caps for the vials of a tray, tray cover 400 can also used independent of individual caps to permit gaseous exchange between the vial contents and environment if so desired. When in place, vial rings 406 telescope over the vial rims of the vials of the tray to help prevent cross-contamination between vial contents. When two or more trays are used in conjunction with a cluster tray of the invention with a nesting lip, such as tray 200 with nesting lip 212 depicted in FIG. 3, tray cover 400 further includes a cover lip 408 extending upwardly from its outer surface to facilitate stacking of a multiplicity of trays. When stacked, cover lip 408 of the tray cover 400 telescopes over the nesting lip of the tray above it.

Now referring to FIGS. 6-9, another alternative embodiment of the present invention is shown and indicated generally by the numeral 500. Cluster tray 500 comprises a plurality of vials 502 removably secured to cluster tray base 504. Vials 502 and base 504 can be thermoformed or injection molded of suitable polymeric materials. Of course, it will be appreciated that the exact number of vials 502 is not critical and a different number of vials 502 may be employed as more suitable for a particular use.

As shown in FIG. 6, tray base 504 has a plurality of tray base regions 506 corresponding to each of the vials 502 of the tray. Each base region 506 is adapted to receive and hold one vial 502 thereon in a manner to allow the later removal of vial 502 from tray base 504 by the user. While the tray base 504 of FIG. 6 is adapted to hold six vials 502, for purposes of clarity, FIG. 6 shows tray base 504 with two vials 502 held thereon, one of which is shown with cap 508 thereon and one of which is shown uncapped.

Tray base 504 has a plurality of base regions 506 each having apertures 510 therethrough and retention means 512 for holding an associated vial 502 thereon. In the preferred embodiment shown in FIGS. 6-7, retention means 512 comprises a plurality of lugs or tabs 514 which cooperate with the associated vial 502 to snappingly and removably hold the vial in base region 506.

Vial 502 is best shown in FIG. 7. Vial 502 has a vial chamber 516 defined by vial bottom 518 and vial wall 520 extending upwardly therefrom. Bottom wall 518 has flange 522 extending outwardly therefrom which cooperates with tabs 514 to provide retention means 512 for holding vial 502 in place on tray base 504. Flange 522, preferably is offset from the plane of bottom wall 518 as shown in FIG. 7 to protect bottom wall 518 from scuffing or scratching contact with a surface when an individual vial 502 is placed thereon.

Vial 502 has removable cap 508 for hermetically sealing vial chamber 516. Cap 502 has sealing lip 524 and cap skirt 526 and is press fit over the open end of vial 502. Preferably, top walls 528 of caps 508 are transparent and have annular rings 530 for nesting engagement with an aperture 510 of tray base 504.

Now referring to FIGS. 8 and 9, alternative preferred embodiments of vials and caps for use with tray base 504 are illustrated. Vial 602 shown in FIG. 8 is analogous to vial 502 except that vial 602 has an upturned flange 604 for easier manipulation of vial 602. The tab of the retention means of an associated tray can be suitably sized to snap over flange 604 or, alternatively, the associated tab may simply clampingly engage flange 604 to hold vial 602 in the associated base region of the tray. Vial 602 is illustrated in FIG. 8 with a cap 608 which is threadably secured thereon, it, of course, being understood that vials can be constructed for use with any selected cap. For example, vial wall 520 of vial 502 can be threaded and used with a threaded cap.

Vial 702 shown in FIG. 9 is of a construction analogous to that of vial 602 except that flange 704 has cut outs therein to allow improved viewing of the contents of vial 702 and, optionally, snap-in retention of vial 702 in an associated base region of a tray.

As will be appreciated by those skilled in the art from the above disclosure, cluster tray 500 provides a tray with removable vials and has many advantageous features. The trays are stackable and vials can be viewed from above or below. Vial bottoms are protected from scratching or scuffing. Vials are hermetically sealed and can be centrifuged individually or on the tray. Vials can stand alone or be in position on the tray and easily viewed.

Suitable materials for the construction of vials and trays of the present invention include moldable transparent polymeric materials, such as polystyrene, polymethyl methacrylate, polyvinylchloride and polyethylene terephthalate, which enable viewing of the contents of the vial without their removal from the vial. Preferred materials include moldable transparent polymeric materials which can also support anchored cell growth for the culture of cells for diagnostic testing, such as polyvinyl chloride and polystyrene pretreated by corona discharge to enhance cell attachment. More preferred materials are polyethylene terephthalate or polyethylene terephthalate glycol which exhibit adequate cell attachment properties without pretreatment of their surface.

Suitable materials for the construction of the vial and tray closures of the invention also include the aforementioned moldable polymeric materials. Preferred moldable polymeric materials are those which can be made transparent such as polystyrene or polyethylene terephthalate to enable viewing of the vial or tray contents without removal of the closure.

The invention has been described with reference to a detailed description of exemplary embodiments. The details of the description are for the sake of example only and are not intended as limitations upon the scope and spirit of the invention.

What is claimed is:

1. An integral array of vials comprising:

a base tray having a plurality of regions, each adapted to receive a vial;

a plurality of vials, each having a bottom wall and an upwardly extending wall defining a vial chamber; and retention means for holding each said vial in an associated region of said base tray, said retention means comprising a flange extending radially outwardly from said vial bottom wall and at least one lug on a said base region engaging said flange.

2. The array of claim 1, wherein said flange has an upwardly turned edge.

3. The array of claim 2, wherein said upwardly turned edge has cut-out areas.

4. The array of claim 1, wherein each said flange has a lower surface for supporting said vial, said lower surface being generally on a single plane, and wherein the outer surface of said bottom wall of each said vial is offset upwardly from the plane of said lower surface of said flange to be thereby spaced from any substantially flat surface on which said vial is placed.

5. The array of claim 1, wherein each said vial is comprised of a transparent polymeric material.

6. The array of claim 5, wherein said transparent polymeric material is polyethylene terephthalate.

7. The array of claim 5 wherein each said region of said base tray has an aperture therethrough generally in visual alignment with a bottom wall of one of said vials.

8. The array of claim 1, wherein each said retention means comprises a plurality of lugs which cooperate with a vial flange to snappingly and removably hold the vial in an associated base region.

9. The array of claim 1, wherein each said vial has cap means for sealing said vial chamber.

10. The array of claim 9 wherein said cap means is comprised of a transparent polymeric material.

11. An integral array of vials comprising:

a base tray having a plurality of regions, each adapted to receive a vial and each of said regions having an aperture therethrough;

a plurality of vials, each having a bottom wall and an upwardly extending wall defining a vial chamber, each said vial being comprised of a transparent polymeric material and having an annular flange extending radially outwardly from said bottom wall; and retention means for selectively removably holding each said vial in an associated region in said base tray, said retention means comprising a plurality of lugs which snappingly engage said flange.

12. The array of claim 11, wherein said flange has an upwardly turned edge.

13. The array of claim 12, wherein said upwardly turned edge has cut-out areas.

14. The array of claim 11, wherein each said flange has a lower surface for supporting said vial, said lower surface being generally on a single plane, and wherein the outer surface of said bottom wall of each said vial is offset upwardly from the plane of said lower surface of said flange to be thereby spaced from any substantially flat surface on which said vial is placed.

15. The array of claim 14, wherein said transparent polymeric material is polyethylene terephthalate.

16. The array of claim 15, wherein each said vial has cap means for sealing said vial chamber.

17. The array of claim 16 wherein said cap means is comprised of a transparent polymeric material.

* * * * *